(12) United States Patent
Ragaller et al.

(10) Patent No.: US 11,215,102 B2
(45) Date of Patent: Jan. 4, 2022

(54) RADIO FREQUENCY SENSOR SYSTEM INCORPORATING MACHINE LEARNING SYSTEM AND METHOD

(71) Applicant: CTS Corporation, Lisle, IL (US)

(72) Inventors: Paul A. Ragaller, Dorchester, MA (US); Alexander G. Sappok, Newton, MA (US); Leslie Bromberg, Sharon, MA (US)

(73) Assignee: CTS Corporation, Lisle, IL (US)

( * ) Notice: Subject to any disclaimer, the term of this patent is extended or adjusted under 35 U.S.C. 154(b) by 541 days.

(21) Appl. No.: 16/247,703

(22) Filed: Jan. 15, 2019

(65) Prior Publication Data

US 2019/0218954 A1    Jul. 18, 2019

Related U.S. Application Data

(60) Provisional application No. 62/618,016, filed on Jan. 16, 2018.

(51) Int. Cl.
*F01N 9/00* (2006.01)
*F01N 3/021* (2006.01)
(Continued)

(52) U.S. Cl.
CPC ............ *F01N 9/002* (2013.01); *F01N 3/021* (2013.01); *F01N 11/00* (2013.01);
(Continued)

(58) Field of Classification Search
CPC .. F01N 9/002; F01N 2560/14; F01N 2560/12; F01N 13/0097; F01N 11/00;
(Continued)

(56) References Cited

U.S. PATENT DOCUMENTS 4,024,452 A    5/1977 Seidel
4,042,879 A    8/1977 Ho et al.
(Continued)

FOREIGN PATENT DOCUMENTS

CN    1032238 A    4/1989
CN    101078692 A    11/2007
(Continued)

OTHER PUBLICATIONS

Rights et al: "Tille Preparation and characterisation of ceria particles," 2013; Retrieved from the Internet: URL:htts:// :: ora.ucc.ie/ bitstream/handle/10468/1141 /MorrisVNA_PhD2013 .pdf.

*Primary Examiner* — Sizo B Vilakazi
(74) *Attorney, Agent, or Firm* — Daniel Deneufbourg

(57) ABSTRACT

A radio frequency sensor system comprising a housing defining a resonant cavity. Radio frequency probe(s) in the cavity transmit and/or receive radio frequency signals. A radio frequency control unit is in communication with the radio frequency probe(s) for determining one or more states of the radio frequency sensor system based on changes in the characteristics of the radio frequency signals. A machine learning system is in communication with the radio frequency control unit for identifying and developing transfer functions and calibrations based on the changes in the characteristics of the radio frequency signals and determining the one or more states of the radio frequency sensor system.

21 Claims, 8 Drawing Sheets

(51) Int. Cl.

| | | |
|---|---|---|
| *G05D 11/13* | (2006.01) | |
| *G01N 7/14* | (2006.01) | |
| *G07C 5/00* | (2006.01) | |
| *F01N 13/00* | (2010.01) | |
| *G01N 15/06* | (2006.01) | |
| *F01N 11/00* | (2006.01) | |
| *G01N 33/00* | (2006.01) | |
| *G01R 1/067* | (2006.01) | |
| *G01N 15/00* | (2006.01) | |
| *G01N 35/00* | (2006.01) | |

(52) U.S. Cl.
CPC ........... *F01N 13/0097* (2014.06); *G01N 7/14* (2013.01); *G01N 15/06* (2013.01); *G01N 33/0006* (2013.01); *G05D 11/13* (2013.01); *G07C 5/008* (2013.01); *F01N 2240/16* (2013.01); *F01N 2550/04* (2013.01); *F01N 2560/12* (2013.01); *F01N 2560/14* (2013.01); *F01N 2900/0402* (2013.01); *G01N 2015/0046* (2013.01); *G01N 2035/00881* (2013.01); *G01R 1/06772* (2013.01)

(58) Field of Classification Search
CPC ................. F01N 3/021; F01N 2550/04; F01N 2900/0402; F01N 2240/16; G05D 11/13; G07C 5/008; G01N 2015/0046; G01N 2035/00881; G01N 33/0006; G01N 15/06; G01N 7/14; G01R 1/06772; Y02T 10/40

See application file for complete search history.

(56) References Cited

U.S. PATENT DOCUMENTS

| | | | |
|---|---|---|---|
| 4,477,771 A | 10/1984 | Nagy et al. | |
| 4,689,553 A | 8/1987 | Haddox | |
| 5,074,112 A | 12/1991 | Walton | |
| 5,103,181 A | 4/1992 | Gaisford et al. | |
| 5,142,595 A | 8/1992 | Chester | |
| 5,157,340 A | 10/1992 | Walton et al. | |
| 5,369,369 A | 11/1994 | Cutmore | |
| 5,423,180 A | 6/1995 | Nobue et al. | |
| 5,447,635 A | 9/1995 | Viscardi et al. | |
| 5,497,099 A | 3/1996 | Walton | |
| 5,500,599 A | 3/1996 | Stange | |
| 5,557,933 A | 9/1996 | Numata et al. | |
| 6,131,386 A | 10/2000 | Trumble | |
| 6,147,503 A | 11/2000 | Nelson et al. | |
| 6,507,308 B1 | 1/2003 | Ono et al. | |
| 6,630,833 B2 | 10/2003 | Scott | |
| 6,819,849 B1 | 11/2004 | Tangonan et al. | |
| 6,854,261 B2 | 2/2005 | Williamson et al. | |
| 7,157,919 B1 | 1/2007 | Walton | |
| 7,357,822 B2 | 4/2008 | Hamahata et al. | |
| 7,679,374 B2 | 3/2010 | Bromberg et al. | |
| 8,384,396 B2 | 2/2013 | Bromberg et al. | |
| 8,384,397 B2 | 2/2013 | Bromberg et al. | |
| 8,889,221 B2 | 11/2014 | Sappok | |
| 9,144,831 B2 | 9/2015 | Sappok et al. | |
| 9,399,185 B2 | 7/2016 | Bromberg et al. | |
| 9,400,297 B2 | 7/2016 | Bromberg et al. | |
| 10,118,119 B2 | 11/2018 | Sappok et al. | |
| 10,260,400 B2 | 4/2019 | Sappok et al. | |
| 2001/0003898 A1 | 6/2001 | Miller et al. | |
| 2001/0007571 A1 | 7/2001 | Murphy et al. | |
| 2002/0005725 A1 | 1/2002 | Scott | |
| 2004/0200198 A1 | 10/2004 | Inoue et al. | |
| 2005/0011278 A1 | 1/2005 | Brown et al. | |
| 2005/0213548 A1 | 9/2005 | Benson et al. | |
| 2005/0241295 A1 | 11/2005 | Breuer et al. | |
| 2006/0027511 A1 | 2/2006 | Brown et al. | |
| 2006/0070373 A1 | 4/2006 | Huang et al. | |
| 2006/0101793 A1 | 5/2006 | Gregoire et al. | |
| 2006/0138082 A1 | 6/2006 | Strang | |
| 2006/0229466 A1 | 10/2006 | Arhancet et al. | |
| 2007/0000218 A1 | 1/2007 | Wirth et al. | |
| 2007/0022746 A1 | 2/2007 | Decou et al. | |
| 2007/0024289 A1 | 2/2007 | Knitt et al. | |
| 2007/0056274 A1 | 3/2007 | Wills | |
| 2007/0068157 A1 | 3/2007 | Kurtz | |
| 2007/0072567 A1 | 5/2007 | Nagai et al. | |
| 2007/0101705 A1 | 5/2007 | Knitt | |
| 2007/0125075 A1 | 6/2007 | Zanini-Fisher et al. | |
| 2007/0125349 A1 | 6/2007 | Zanini-Fisher et al. | |
| 2007/0130923 A1 | 6/2007 | Dye et al. | |
| 2007/0169469 A1 | 7/2007 | Knitt | |
| 2007/0209333 A1 | 9/2007 | Kondou | |
| 2007/0214862 A1 | 9/2007 | Kubinski et al. | |
| 2008/0018442 A1 | 1/2008 | Knitt | |
| 2008/0059093 A1 | 3/2008 | Bromberg et al. | |
| 2008/0066621 A1 | 3/2008 | Naito et al. | |
| 2008/0092499 A1 | 4/2008 | Otsuka et al. | |
| 2008/0110143 A1 | 5/2008 | Chen et al. | |
| 2008/0264036 A1 | 10/2008 | Bellovary | |
| 2009/0038294 A1 | 2/2009 | Anderson et al. | |
| 2009/0295509 A1 | 12/2009 | Master et al. | |
| 2010/0101409 A1 | 4/2010 | Bromberg et al. | |
| 2010/0102828 A1 | 4/2010 | Bromberg et al. | |
| 2012/0138093 A1 | 6/2012 | Sappok et al. | |
| 2012/0235865 A1* | 9/2012 | Nath ................. H04W 64/00 342/451 |
| 2013/0072924 A1 | 3/2013 | Burgener et al. | |
| 2013/0125745 A1 | 5/2013 | Bromberg et al. | |
| 2013/0127478 A1 | 5/2013 | Bromberg et al. | |
| 2013/0298530 A1 | 11/2013 | Carlill et al. | |
| 2014/0087769 A1* | 3/2014 | Nath ................. H04W 64/00 455/456.6 |
| 2014/0116028 A1 | 5/2014 | Sappok et al. | |
| 2014/0199950 A1* | 7/2014 | Ash, Jr. .............. H01Q 1/50 455/77 |
| 2014/0227980 A1* | 8/2014 | Esselink ............. G07B 15/00 455/73 |
| 2015/0123688 A1 | 5/2015 | Sappok et al. | |
| 2015/0132187 A1 | 5/2015 | Takaoka et al. | |
| 2015/0355110 A1 | 12/2015 | Sappok et al. | |
| 2015/0358091 A1* | 12/2015 | Sappok ............... F01N 11/00 455/67.11 |
| 2016/0109425 A1 | 4/2016 | Sappok et al. | |
| 2017/0182447 A1* | 6/2017 | Sappok ............... F01N 3/021 |
| 2017/0211453 A1 | 7/2017 | Sappok et al. | |
| 2018/0137695 A1 | 5/2018 | Sappok et al. | |
| 2019/0070547 A1* | 3/2019 | Sappok ............... F01N 11/00 |

FOREIGN PATENT DOCUMENTS

| | | |
|---|---|---|
| CN | 103841914 A | 6/2014 |
| DE | 3317215 A1 | 11/1983 |
| DE | 102004016725 A1 | 2/2006 |
| EP | 0097416 A1 | 1/1984 |
| EP | 0356040 A2 | 2/1990 |
| JP | 62-95443 A | 5/1987 |
| JP | 3-205543 A | 9/1991 |
| JP | 4-505665 A | 10/1992 |
| JP | 2008-231932 A | 10/2008 |
| JP | 2011-14579 A | 1/2011 |
| JP | 2012-507660 A | 3/2012 |
| WO | 92/02807 A1 | 2/1992 |
| WO | 93/05388 A1 | 3/1993 |
| WO | 00/50743 A1 | 8/2000 |
| WO | 2004/074670 A2 | 9/2004 |
| WO | 2005/060653 A2 | 7/2005 |
| WO | 2005/093233 A1 | 10/2005 |
| WO | 2006/002037 A2 | 1/2006 |
| WO | 2007/130896 A2 | 11/2007 |
| WO | 2009031600 A2 | 3/2009 |
| WO | 2010/074812 A1 | 7/2010 |
| WO | 2011/156477 A2 | 12/2011 |
| WO | 2014064406 A1 | 5/2014 |

(56) References Cited

FOREIGN PATENT DOCUMENTS

| WO | 2015/188188 A1 | 12/2015 |
| WO | 2015/188189 A1 | 12/2015 |
| WO | 2017/165220 A1 | 9/2017 |

* cited by examiner

| Class No. | Dataset | Training Size | | Testing Size | | Accuracy |
|---|---|---|---|---|---|---|
| 1 | Uniform | 3132*89 | | 783*89 | | |
| 2 | Center | 2032*89 | | 508*89 | | |
| 3 | Outer | 1024*89 | 9852*89 | 256*89 | 2463*89 | 100% |
| 4 | Semi-cylinder | 1860*89 | | 465*89 | | |
| 5 | Bilateral | 1804*89 | | 451*89 | | |

RADIO FREQUENCY SENSOR SYSTEM INCORPORATING MACHINE LEARNING SYSTEM AND METHOD

CROSS-REFERENCE TO RELATED APPLICATIONS

This patent application claims priority and benefit of the filing date of U.S. Provisional Patent Application Ser. No. 62/618,016 filed on Jan. 16, 2018, the disclosure and contents of which is expressly incorporated herein in its entirety by reference.

FIELD OF THE INVENTION

This invention relates generally to a radio frequency sensor system and method and, more particularly, to a radio frequency sensor system and method incorporating a machine learning system for developing RF sensor transfer functions and calibrations for a given data set.

BACKGROUND OF THE INVENTION

As exhaust and pollution regulations on commercial and passenger vehicles become more stringent, there is an increasing need for robust and reliable controls for the aftertreatment devices used to meet the regulations. More precise and reliable measurements of the operative state(s) of these devices are crucial enablers in the precise control and diagnosis of these systems.

Operation of these systems at the extremes of their capability requires real-time measurements of the state(s) of the system. Further, as the performance of these systems are pushed to their extremes, possible failure of these systems becomes a concern. In addition, concerns about real driving emissions, from light, medium and heavy-duty vehicles in urban environments have raised concerns motivating tighter emission controls and real-time measurements and diagnostcis.

Modern emission aftertreatment control systems consist of a number of various different components including filters, catalysts, fluid delivery systems, thermal management systems, and a complex network of sensors and controls. Currently, only discrete sensors are available that provide measurements of one or, at most, two properties of the exhaust gas at specific discrete locations in the exhaust system. Furthermore, these systems are not capable of directly monitoring the state of the filter, catalyst, or related sub-system, but rather only monitor the exhaust gas properties upstream or downstream of the system, such as upstream or downstream of a catalyst or filter in one example.

It is desirable to utilize a single measurement system, such as a radio frequency sensor, to monitor a plurality of exhaust system variables or parameters in order to improve control of the system and detect various faults, failure conditions, or noise factors.

The challenge of using a single measurement system to simultaneously monitor multiple exhaust system variables or parameters lies in the calibration of the system and development of transfer functions, detection methods, and correlations which may be used to relate changes in the measured RF signal to changes in one or more states of the system.

Currently, the RF sensor calibrations rely on manual methods to analyze the frequency resonance curves/modes and identify (based on a set of predefined criteria) regions in the frequency resonance curves/modes suitable for calibration.

These types of spectral resonant curve/mode analysis techniques involve an iterative trial and error process, in one example, first identifying specific frequency regions, then computing a number of parameters derived from either the magnitude or frequency or phase signal, then evaluating the correlation and/or monotonicity or the response of the identified parameters to the known reference state of the system.

Alternative calibration approaches rely on expert systems, such as simulations and models, to provide an expected RF signal response a priori to guide the calibration. Both methods have drawbacks. The first is cumbersome, time consuming, and oftentimes does not lead to an optimal solution, given the manual nature of the process. The second method requires significant effort and investment to develop and validate the models and simulation tools, which are not always available for each application. The current approaches are therefore limited to developing correlations or calibration functions for a small handful of parameters at best, and require significant time and resources to fully-develop and validate, oftentimes leading to a sub-optimal solution.

The present invention is directed to the use of a machine learning system in communication with the control unit of the RF sensor system to develop these calibrations, as well as identify various system conditions or anomalies, will allow for a substantial reduction in time and resources spent in calibration development, as well as lead to a more accurate and robust calibration. Furthermore, this approach enables additional system noise factors or failure modes to be identified and detected, which is not always possible using either a manual or model-based approach. In some cases the detection of failures or signs of system degradation are useful for diagnostic systems, such as on-board diagnostics.

SUMMARY OF THE INVENTION

The present invention is directed to a radio frequency sensor system comprising a housing defining a radio frequency resonant cavity, one or more radio frequency probes in the cavity of the housing for transmitting and/or receiving radio frequency signals, a radio frequency control unit in communication with the one or more radio frequency probes for determining one or more states of the radio frequency sensor system based on changes in the characteristics of the radio frequency signals, and a machine learning system in communication with the radio frequency control unit for identifying and developing transfer functions and calibrations signals and determining the one or more states of the radio frequency sensor system based on the changes in the characteristics of the radio frequency signal.

In one embodiment, the state of the radio frequency sensor system is determined based on changes in the amplitude and/or shifts in the frequency and/or shifts in the phase of the radio frequency signals, the machine learning system identifying and developing transfer functions and calibrations based on the changes in the amplitude and/or shifts in the frequency and/or shifts in the phase of the radio frequency signals.

In one embodiment, the radio frequency signals are transmitted and/or received over a broad frequency range for establishing one or more resonant modes, with the machine learning system identifying and developing transfer functions and calibrations based on changes in the characteristics of the one or more resonant modes.

In one embodiment, the radio frequency control unit is adapted to generate data in response to the changes in the characteristics of the radio frequency signals that are representative of the one or more states of the radio frequency sensor system and the machine learning system includes a neural network comprising an input for the data, a processing unit for the data, and a numeric output representative of the one or more states of the radio frequency sensor system.

In one embodiment, the system further comprises a retentate filter or a catalyst in the cavity of the housing, the radio frequency control unit being adapted to generate data in response to the changes in the characteristics of the radio frequency signal representative of changes in the state of the retentate filter or the catalyst.

In one embodiment, the radio frequency control unit is adapted to generate data in response to the changes in the characteristics of the radio frequency signal representative of changes in the distribution of retentate or exhaust constituents in the retentate filter or the catalyst respectively.

In one embodiment, the system further comprises means for training the neural network to down-select one or more radio frequency sensor system parameters selected from temperature, flow rate, radio frequency resonance modes, radio frequency phase curves, or system operating state.

In one embodiment, the system further comprises dimensionality reduction means for simplifying the machine learning system transfer functions and calibrations.

In one embodiment, the system further comprises means associated with the machine learning system for down-sampling a whole set of the data generated by the radio frequency control unit prior to feature selection.

In one embodiment, the system further comprises means for developing the machine learning system transfer functions and calibrations prior to or during the operation of the system.

The present invention is also directed to a method of operating a radio frequency sensor system including a housing defining a radio frequency resonant cavity, one or more radio frequency probes in the cavity of the housing for transmitting and/or receiving radio frequency signals, and a radio frequency control unit in communication with the one or more radio frequency probes for determining one or more states of the radio frequency sensor system based on changes in the characteristics of the radio frequency signals comprising the step of providing a machine learning system in communication with a radio frequency control unit for identifying and developing transfer functions and calibrations and determining one or more states of the radio frequency system based on changes in the characteristics of radio frequency signals transmitted and/or received in a cavity of the radio frequency sensor system.

In one embodiment, the state of the radio frequency sensor system is determined based on changes in the amplitude and/or shifts in the frequency and/or shifts in the phase of the radio frequency signals, the machine learning system identifying and developing transfer functions and calibrations based on the changes in the amplitude and/or shifts in the frequency and/or shifts in the phase of the radio frequency signals.

In one embodiment, the radio frequency signals are transmitted and/or received over a broad frequency range for establishing one or more resonant modes, the machine learning system identifying and developing transfer functions and calibrations based on the changes in the characteristics of the one or more resonant modes.

In one embodiment, the radio frequency control unit is adapted to generate data in response to the changes in the characteristics of the radio frequency signals that are representative of the one or more states of the radio frequency sensor system and the machine learning system includes a neural network comprising an input for the data, a processing unit for the data, and a numeric output representative of the one or more states of the radio frequency sensor system.

In one embodiment, a retentate filter or a catalyst is in the cavity of the radio frequency sensor system, the radio frequency control unit being adapted to generate data in response to the changes in the characteristics of the radio frequency signal representative of changes in the state of the retentate filter or the catalyst.

In one embodiment, the radio frequency control unit is adapted to generate data in response to the changes in the characteristics of the radio frequency signal representative of changes in the distribution of retentate or exhaust constituents in the retentate or the catalyst respectively.

In one embodiment, the method further comprises the step of training the neural network to down-select one or more radio frequency sensor system parameters selected from temperature, flow rate, radio frequency resonance modes, radio frequency phase curves, or system operating state.

In one embodiment, the method further comprises the step of dimensional reduction for simplifying the machine learning system transfer functions and calibrations.

In one embodiment, the method further comprises the step of down-sampling a whole set of the data generated by the radio frequency control unit prior to feature selection.

In one embodiment, the method further comprises the step of developing the machine learning system transfer functions and calibrations prior to or during the operation of the system.

The present invention is further directed to a radio frequency sensor system comprising a housing defining a radio frequency resonant cavity, one or more radio frequency probes in the cavity of the housing for transmitting and/or receiving radio frequency signals, a radio frequency control unit in communication with the one or more radio frequency probes and adapted to generate data for determining one or more states of the radio frequency sensor system based on changes in the amplitude and/or shifts in the frequency and/or shifts in the phase of the radio frequency signals, and a machine learning system in communication with the radio frequency control unit and including a neural network with an input for the data generated by the radio frequency control unit, a data processor, and an output, the machine learning system being adapted for identifying and developing transfer functions and calibrations and determining the one or more states of the radio frequency sensor system based on the changes in the amplitude and/or shifts in the frequency and/or shifts in the phase of the radio frequency signals.

Other advantages and features of the present invention will be more readily apparent from the following detailed description of the preferred embodiment of the invention, the accompanying drawings, and the appended claims.

BRIEF DESCRIPTION OF THE DRAWINGS

These and other features of the invention can best be understood by the description of the accompanying FIGS. as follows.

DESCRIPTION OF THE EMBODIMENT

Figure 1:
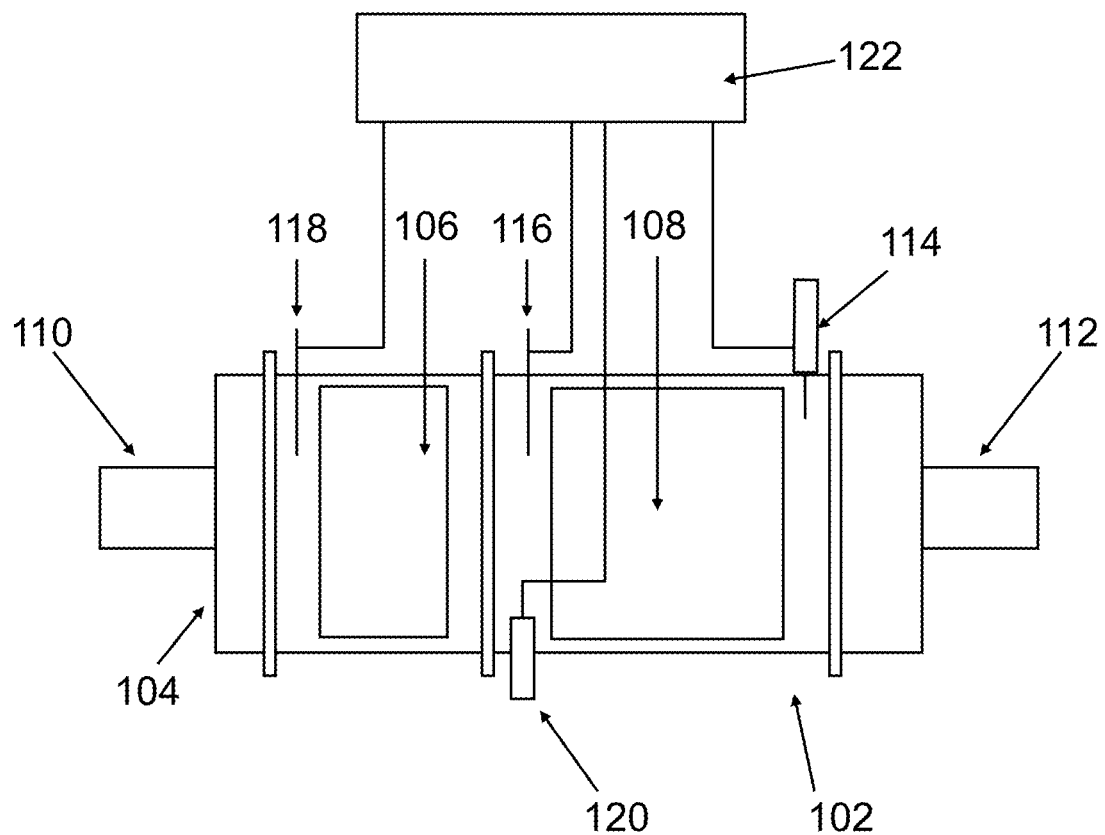
FIG. 1 is a simplified schematic of an emissions aftertreatment RF sensor system including an RF sensor machine learning system and method in accordance with the present invention.

Radio frequency (RF) sensors have been developed to measure retentate levels accumulated in filters and changes in the loading state of for example vehicle emission aftertreatment catalyst systems, among others. The applications for these measurements has been extended to include soot and ash measurements in for example vehicle emission aftertreatment diesel particulate filter (DPF) and gasoline particulate filter (GPF) systems, ammonia adsorption measurement on selective catalytic reduction (SCR) systems, oxygen storage in three-way-catalyst (TWC) systems, and has potential to measure other systems where a change in the loading level of a specific material constituent changes within a cavity, thus resulting in a measurable change in the cavity's bulk dielectric constant. Global measurements have historically utilized one or more parameters isolated from the full spectral measurement (either in magnitude or phase), as described in for example the following U.S. Pat. Nos. 7,679,374; 8,384,396; 8,384,397; 9,399,185; and 9,400,297.

During operation, the RF sensor, via the control unit thereof, scans over a broad frequency range—sending and receiving radio frequency signals. The section of the spectrum that is scanned can be continuous, or it can be multiple but separate regions of the spectrum. It can be scanned continuously, or it can be scanned intermittently, with a duty cycle that is determined by the software and which can be adjusted according to the need or the system operating conditions.

The strength of the signal returning compared to the sent signal (magnitude) as well as the phase or frequency shift between the sent and received signals may be measured over a given frequency range. A result of sweeping over a broad frequency range is that multiple resonances or resonant modes or curves may be established or generated which are functions of the geometry and dielectric constant of the system housing cavity and its contents. As such, these are eigenmodes of the system itself, where each eigenmode corresponds to a specific geometric mode shape. Each mode shape has areas of high and low electric field that effectively probe different areas of the cavity.

The present invention relates to a system and method of efficiently processing the full spectral data set or resonance curves or modes, in one example, acquired by the control unit of the RF sensor, through the use of machine learning techniques, in order to develop accurate and robust sensor transfer functions and calibrations useful for both control and diagnosis of the RF emissions aftertreatment sensor system.

In another example, the data may or may not include resonance, but may include one or more frequency points sufficient to develop a unique calibration or set of correlations for a particular application. This method involves the incorporation of machine learning system means for training a model or computational framework with a given data set associated with known reference conditions, but with the limited knowledge of the system or its response a priori.

The model may be a generalized model, and need not be specific to the particular application. Through the application of machine learning means/techniques, correlations and transfer functions may be developed, or patterns recognized in the data which may be useful to relate a specific change in the RF signal to a known state or condition of the aftertreatment system.

A number of factors may impact the resulting RF sensor control unit measurements as well as the state of the aftertreatment system in practical applications, which include but are not limited to:

1. Change in the independent variable or variables (such as composition, quantity, or the like) being monitored by RF sensing;

2. A fault, failure, or anomalous or abnormal operation or occurrence within the system or its environment; and 3. The influence of external noise factors or extraneous inputs that impact the RF measurement but are not themselves the independent variable or variables being monitored.

One illustrative example of the items listed above include the application of RF sensing to diesel or gasoline particulate filter aftertreatment systems. In this example, the independent variable monitored by the RF sensor may be the level of soot or ash in the filter. During the course of normal operation, faults, failures or malfunctions may occur, such as damage to the filter element itself (cracking or melting), changes to the filter structure, deformation of the filter housing or cavity, extreme operating or environmental conditions, or the introduction of abnormal foreign material onto the filter, for example.

Noise factors may include a change in the temperature of the filter or the ambient environment, water storage, environmental variables, the spatial distribution of the soot or ash in the filter, the chemical composition or physical properties of the soot or ash in the filter, or the composition and characteristics of the exhaust gases flowing through the filter, or the current or historical operating state of the system, among others.

In another example, the system monitored by RF sensing may be a catalyst emissions aftertreatment system and the independent variable may be the level of or quantity of a gas species stored or adsorbed on the catalyst such as the level of NOX, O2, NH3, HC, or CO or CO2, sulfur, phosphorous, lead, silicon compounds or any other gas species or solid/liquid (such as water) or contaminant material stored or collected on the catalyst.

In this case, a fault or malfunction may relate to a loss of catalyst performance or storage capacity, chemical or physical changes to the system including structural defects or failures, or anomalous changes in the state of the system such as by sintering or deactivation through extreme temperature events or poisoning.

System noise factors in this case may include aging of the catalyst (either on the entire volume or in local regions within the catalyst), deposition of foreign material such as sulfur, phosphorous or other compounds on the system, influence of temperature, humidity, flow, or related changes in exhaust gas properties or the environment, or even the operation of the upstream system such as the engine, among other noise factors. It should be noted that parameters or conditions considered to be noise factors in one application may be considered as faults or failures in another application, and vice versa.

Similarly, the system monitored need not be a filter or catalyst but may be any relevant component or sub-system suitable for the application of RF sensing, such as tanks, vessels, chemical reactors, or conduits where one or more independent variables may be identified for measurement with the RF sensor, and any number of noise factors or fault conditions may be identified which may also influence the signal. In one exemplary embodiment, the tank or vessel may be a fuel tank, lubricant reservoir, or urea tank.

Manual inspection of the RF resonance curve or mode may not readily allow for each of the many individual effects of the noise factors, failure modes or fault conditions, or changes in the independent variable(s) to be precisely ascertained such that a robust calibration, transfer function, or detection method may be determined. Such a transfer function or detection method is required to relate specific changes in individual features in the measured amplitude, frequency, or phase signal (or a derivative thereof) to the underlying physical or chemical changes to the system such that these conditions can be detected in situ during normal operation of the system.

The present invention overcomes these difficulties by incorporating a machine learning system in communication with the control unit of the system to efficiently process the RF signal measurements including for example changes in the amplitude and/or shifts in the frequency and/or shifts in the phase of the radio frequency signals and identify correlations between the RF signal characteristics and the independent variables (1), faults (2), and noise factors (3) in order to develop accurate and robust transfer functions and calibrations and determining one or more states of the radio frequency sensor system.

FIG. 1 depicts one embodiment 102 of an emissions aftertreatment RF sensor system incorporating a machine learning/neural network system and method in accordance with the present invention.

FIG. 1 depicts a filter or catalyst housing 104, however any suitable conduit, housing, or tank may be used which serves as and defines an interior RF waveguide or resonant cavity. Conduits 110 and 112 provide a fluid connection from the housing 104 to the rest of the exhaust system. Conduit 110 is the input connection delivering exhaust from the engine to the housing 104 and conduit 112 is the outlet conduit. The housing 104 contains one or more catalysts or filters 106 and 108.

One or more RF probes or antennas 114 are installed on housing 104 to transmit and/or receive radio frequency signals within the cavity of the housing 104. The RF signals propagate through the cavity and the catalysts or filters 106 and 108 in the cavity thereby allowing for direct measurement of the state of the catalysts or filters 106 and 108. The system 102 includes additional sensors 116, 118, and 120 which may be temperature sensors, pressure sensors, gas sensors, or the like.

A control unit 122 is in communication with one or more sensors or elements 114, 116, 118, or 120 for determining one or more states of the radio frequency sensor system based on changes in the characteristics of the radio frequency signals. Control unit 122 may be a smart sensor in one example, or an engine or aftertreatment control unit in another example. The communication may be analog or digital, or some combination.

In one example, the communication may use a controller area network (CAN). In another example, control unit 122 may directly send and receive radio frequency signals to or from probe 114 via a coaxial connection. The control unit 122 may contain one or more microcontrollers, memory, signal conditioning circuits, radio frequency signal generating and receiving circuits (such as synthesizers and magnitude or phase detectors), and other related components. The control unit 122 may include a microcontroller to process the transmitted and/or received signals utilizing a machine learning system.

In another example, the control unit 122 may be in communication with another control unit (not shown) such as for example a master control unit or an engine control unit. In this example, the control unit 122 or the master control unit may be utilized to apply machine learning techniques to the sensor data.

In another example, the control unit 122 or some other control unit in communication with control unit 122 communicates wirelessly such as over Wi-Fi or a cellular network with a central server. The central server aggregates data from many control units such as 122, and from many applications, apply machine learning techniques to this aggregated database, such as a cloud database, and provide period "over-the-air" updates to control unit 122 or another control unit to which control unit 122 is connected or in communication with.

In this manner, computationally intensive machine learning models and techniques may be applied offline in a data center or other computational facilities and only the resulting output, such as transfer functions, calibration algorithms, weight and bias arrays, equations, or look up tables and the like are programmed to control unit 122 or a master control unit in communication with control unit 122.

Control unit 122 may be installed on many different vehicles or fleets of vehicles. Data from all of these vehicles may be provided to the central server for application of the machine learning techniques. Results of the application of machine learning to the aggregate data set may be distributed back to the vehicles. This process of training a machine learning model using data from multiple vehicles or systems may occur during normal development phase or as part of a dedicated sensor calibration activity (factory calibration), or may be carried out once the vehicles or systems are in-actual in-use operation, so-called self-calibration. In another example, the machine learning approach need not be carried out on a central server of computer but rather on the control unit 122 itself.

An example of the RF measurements which may be obtained from the emissions aftertreatment system housing or cavity 104 are shown in FIG. 2.

Figure 2A:
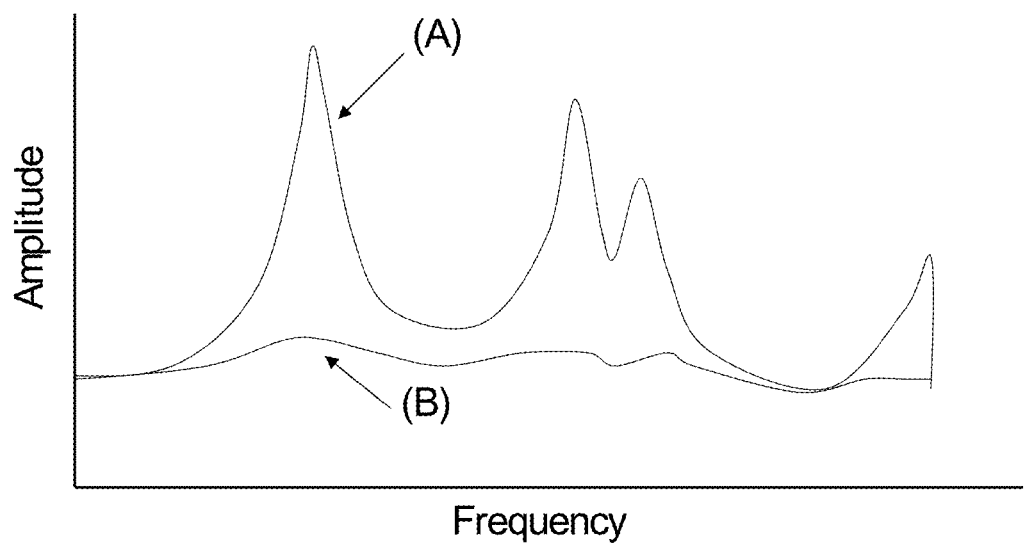
FIGS. 2A and 2B are graphs depicting examples of the RF signal amplitude and phase measurements obtained from the resonant cavity of the emissions aftertreatment RF sensor system shown in FIG. 1.
Figure 2B:
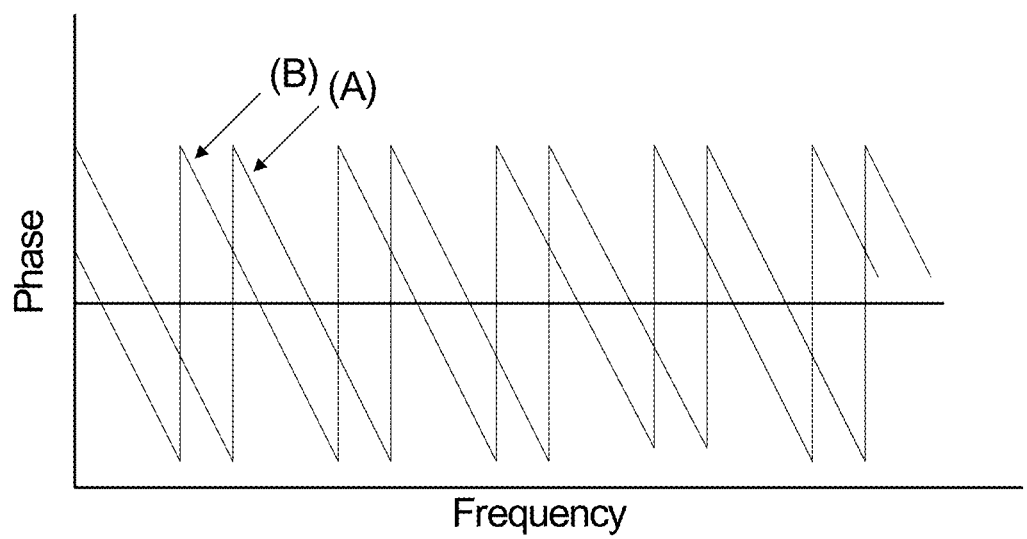

FIG. 2A shows the amplitude measurements as a function of frequency and FIG. 2B shows the phase measurements as a function of frequency for a system 102 with two RF antennas 114.

Two different curves (A) and (B) are also shown in FIG. 2A and FIG. 2B, however any number of curves may be acquired. Each curve in FIG. 2A and FIG. 2B corresponds to a different system state, such as states (A) and (B). In practical applications there may be any number of curves corresponding to any number of states. In some cases, specific features of the various curves corresponding to different states may overlap, such that specific regions of curves corresponding to multiple different system states may be the same, however it is desirable to identify unique features or characteristics of the curves (parameters derived from the magnitude, frequency, and phase data) shown in FIG. 2A and FIG. 2B, and relate those features to uniquely identify each system state for various frequency ranges.

Furthermore, in the case of RF cavity resonance measurements, each resonant mode (identified as a peak in the magnitude spectrum shown in FIG. 2A) is related to a specific electric filed distribution within the housing or cavity 104.

FIGS. 3A-3D illustrate four different electric field distributions in the housing or cavity 104 of an RF emissions aftertreatment sensor system 102 containing two RF antennas 114. Depending on the resonance frequency, different cavity modes may be excited, with each mode exhibiting peaks and nulls in different spatial regions of the cavity. Regions in which the electric field is strong (identified as dark shaded regions in FIGS. 3A-3D) provide a high degree of sensitivity to monitor local changes in the region of strong field relative to other regions within the cavity 104 where the field is weak (light shaded regions in FIGS. 3A-3D).

In this manner, the relative spatial distribution or local variations within the cavity 104 may be monitored by monitoring the response of multiple resonant modes. It is further desirable to relate changes in the resonance mode or curve structure to the specific spatial region within the cavity 104 responsible for the change in the cavity resonance response.

Figures 3A, 3B, 3C, 3D:
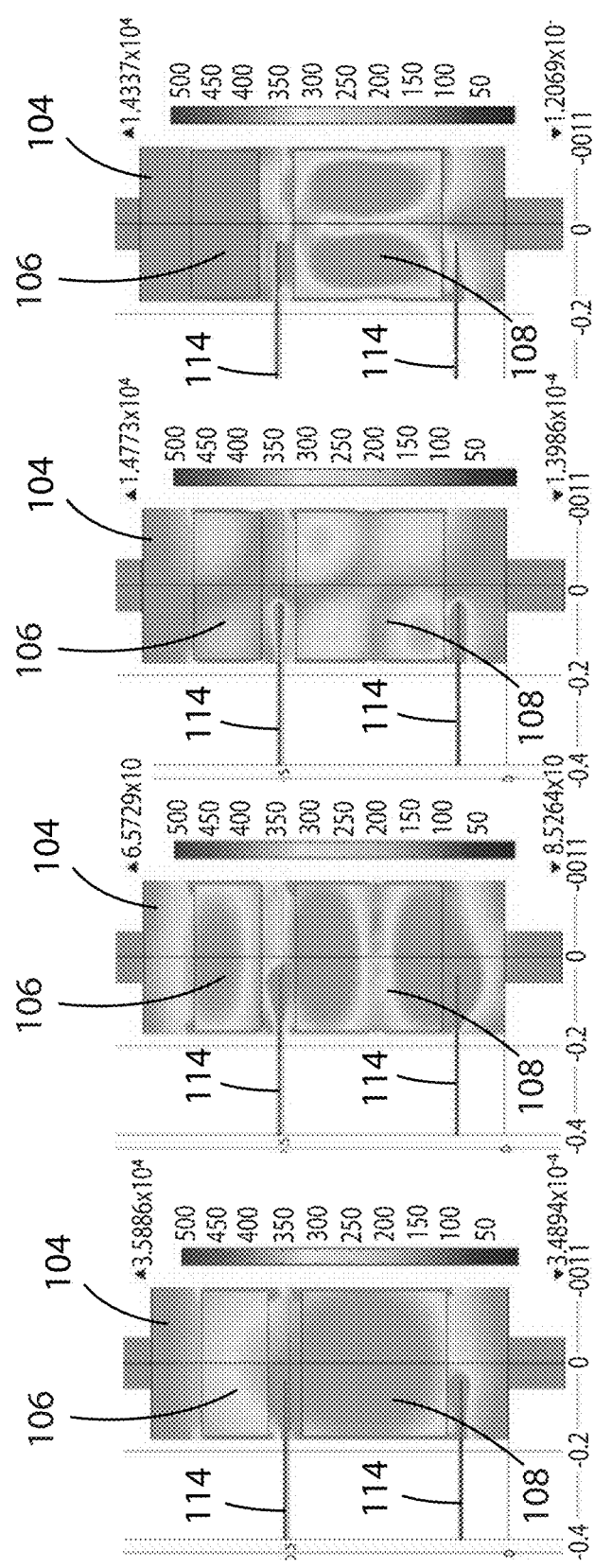
FIGS. 3A-3D depict four example electric field distributions in the cavity of the emissions aftertreatment RF sensor system shown in FIG. 1.
Figure 4A:
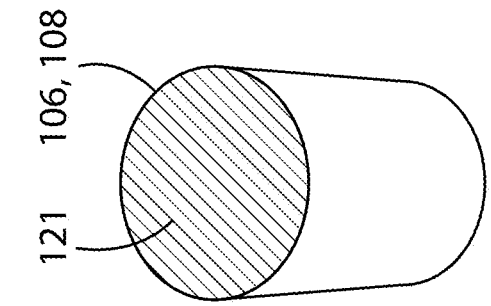
FIGS. 4A-4E depict examples for the distribution of retentate in the retentate filter of the emissions aftertreatment RF sensor system of FIG. 1.
Figure 4B:
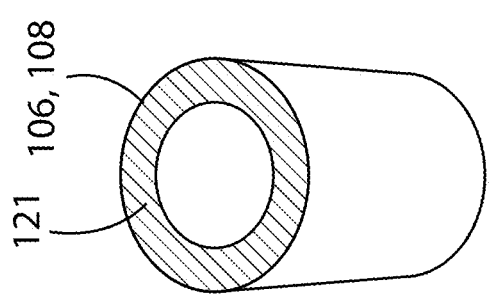
Figure 4C:
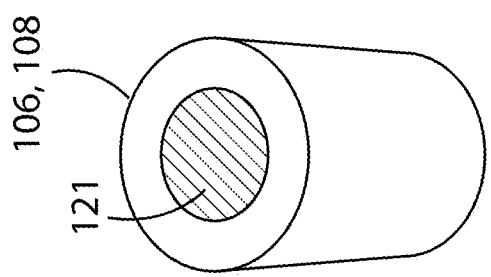
Figure 4D:
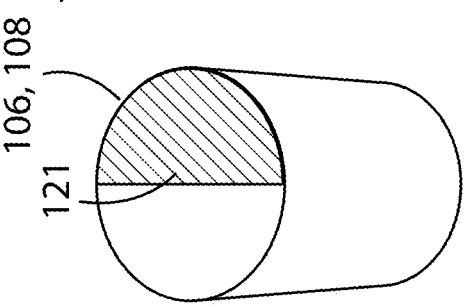
Figure 4E:
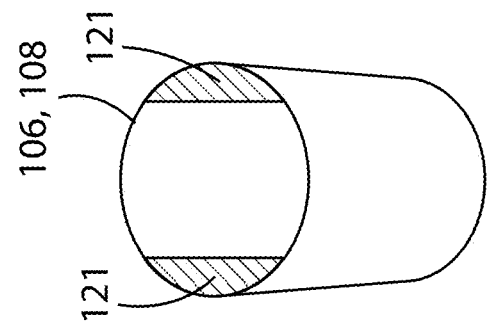

The first mode or fundamental, shown in FIG. 3A, appears as a peak in the magnitude spectrum at the lowest frequency. Its specific mode shape has an area of high electric field in the center of the cavity 104. The next mode shown in FIG. 3B, which references the peak at a higher frequency, has areas of high electric field at the front and back and center of the cavity 104. As the frequency and mode number increase, the mode shapes become geometrically more complex, as shown in FIG. 3C and FIG. 3D. At much higher frequencies, the mode shapes even begin to incorporate a radial component where the high electric field probes primarily the outside edge of the cavity 104. Other modes would primarily probe the central region of the cavity 104.

In one particular example for a typical RF calibration development in the case of a soot filter 106 or 108 in the cavity 104 of the system 102, the calibration may be designed to incorporate a single statistic (derived from the magnitude or phase signal) from the spectrum that includes information from multiple resonance modes. This allows for a reliable measure of the global level of retentate (soot, ash, or the like) 121 in the filter 106 or 108 of the system 102.

However, if the retentate 121 forms a nonuniform distribution, some of the resonance modes are affected differently from those conditions where the retentate 121 is homogenously distributed through the filter 106 or 108.

For example, where the soot 121 in the filter 106 or 108 is located around the outer edge of the filter 106 or 108 only, the higher frequency modes that have a high electric field strength at the edge of the filter 106 or 108 may be affected more than modes whose electric field is strong at the center and weak at the edge of the filter 106 or 108.

In another example such as ammonia storage on a selective catalytic reduction (SCR) system, the storage of the ammonia may vary axially or radially. As such, by keeping an inventory of the relative changes to each of the modes, it is possible to detect and categorize these distributions.

In many instances, the relative change in modes is difficult to observe, and the transfer functions and calibrations required to track and compute these changes become prohibitively complex.

The system and method of the present invention incorporates a machine learning system and method with models trained to recognize the spectral features that represent these distributions in the case of a filter 106 or 108, or to detect faults, malfunctions, or detect and compensate for noise factors in another example. In yet another example, the machine learning system and method relate changes in the RF signal to one or more independent variables being monitored.

Figure 7:
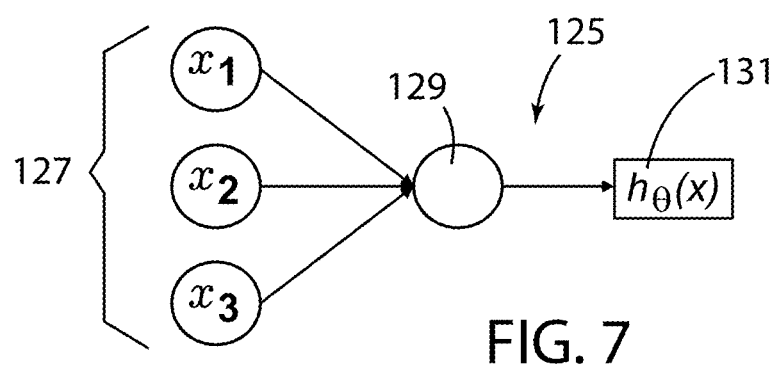
FIG. 7 is a schematic of one of the neurons of the neural network of the machine learning system of the emissions aftertreatment RF sensor system of the present invention.

A simple schematic of one of the neurons 125 of the neural network of the machine learning system is represented in FIG. 7 and consists of three parts: the input/input layer 127, the processor/processing unit 129, and the output/output layer 131. Inputs are determined from features in the raw RF data generated and collected by the RF control unit 122 in response to changes in the characteristics of the radio frequency signals transmitted/received by the RF control unit 122 and are fed into the processing unit 129. The processing unit 129 performs a mathematical operation on the input 127 to generate the output 131.

The neuron 125 may be stacked into multiple layers, with each layer containing multiple neurons 125 to create and define a neural network. The size and number of layers may be customized to the specific application and dataset.

The outputs from the multiple neurons 125 defining the neural network are combined to provide an output of the required measurement.

In one example, this final output/output layer may provide a categorical output. This is especially useful in classifying different cases, such as the soot distributions in the filter 106 or 108 of the system 102 as shown in FIGS. 4A-4E. The output layer 131 however may be modified to provide a continuous, numerical output via one of several methods.

In one example, the output/output layer 131 may give the relative probability that the measurement falls within a particular category. In the case where these categories are numeric, the probabilities may be combined to provide a continuum result.

In another example, the output layer 131 may be modified to provide a regressive result. In this case, known as a General Regression Neural Network (GRNN), the output is provided directly as a continuum value rather than as a categorical one.

The GRNN output is represented below where Y(x) is the predicted value given the measurement x, $y_k$ is an activation weight for the neuron k, and K(x, xk) is typically a Gaussian kernel basis function:

$$Y(x) = \frac{\sum_{k=1}^{N} y_k K(x, x_k)}{\sum_{k=1}^{N} K(x, x_k)}$$

In this way, application of the neural network algorithm may be expanded beyond categorization to include numeric measurement, such as the quantity of ammonia adsorption on an SCR catalyst 106 or 108, or the amount of ash accumulation in a DPF/GPF filter 106 or 108.

Figures 8, 9:
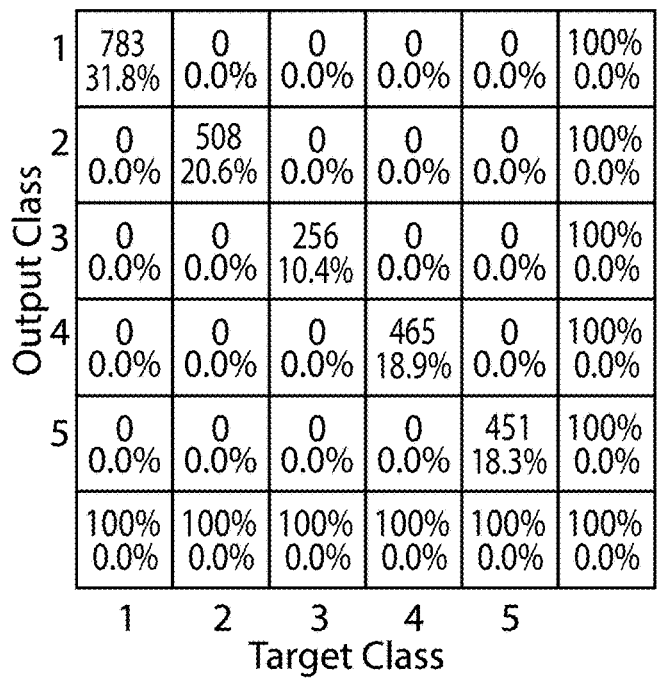
FIG. 8 is a chart including a summary of the RF data used to train and test the neural network of the machine learning system of the emissions aftertreatment RF sensor system of the present invention.
FIG. 9 is a confusion matrix chart summarizing the output of the neural network of the machine learning system of the emissions aftertreatment RF sensor system of the present invention.

The ability to provide a fully numeric output 131 allows for optimization of both sensor calibration processes and sensor accuracy, as shown in FIG. 8. Since they utilize the most influential parameters of the whole spectral measurement, neural networks with probabilistic or general regression numeric output enable the increased accuracy and rejection of signal noise and other confounding sources.

In the case of the RF sensor system 102, features based on the characteristics of the raw magnitude and phase spectra or some derivative function thereof, as shown in FIGS. 2A and 2B, are utilized to generate the input/input layer 127. Raw data are then collected at each system state. These states are defined in advance, based on the desired output 131, and are categorized numerically, which is a way to allow the neural network to provide a numeric output corresponding to each state. System states may comprise discrete categories or can be composed of a continuum of states that define a single output parameter. The raw data measurements, along with the category assigned for that system state, are used to train the processing layers of the neural network.

From raw data in the input layer 127 to a final output 131, the neural network computes the results in sequence. This can take the form of:

$$h_\Theta(x) = X \cdot [\Theta_1, \Theta_2, \ldots, \Theta_n]$$

where X is the input, $\Theta_i$ is the weighting matrix for each layer, n is the number of layers, and h is the output. This training process adjusts the weighting matrices that make up the processing layers of the neural network. The size of the neural network depends heavily on the application and the desired accuracy of the output 131. While the number of inputs 127 is defined by the data, the dimension of the weighting matrix may be varied to include a number of input nodes that differ from X, and with any number of hidden (processing) layers, $\Theta_i$. The data collected at each state, along with the category, is used to minimize the error of the output by adjusting, or training, the weighting matrix. After training is complete, new RF data is inputted to the neural network and an output computed without the need for further training. In this way, new data may be tested through the neural network.

In one example, there may be a need to decipher between a uniform retentate distribution and a nonuniform retentate distribution in the filter 106 or 108 in the cavity 104 of the system 102. The retentate may be any solid, liquid, or gas in this case that is stored in or removed from the cavity 104 or the filter 106 or 108 at any point in time. To train the neural network, raw data is obtained for distributions that are known or assumed to be either uniform or nonuniform. The data used in the analysis is measured in the system by appropriately adjusting the distribution of the retentate within the cavity 104, and adjusting the sources of noise (such as temperature or composition of the exhaust, in one example). However, in some cases, the data is synthesized from modeling of the unit with known dielectric properties of the retentate.

In this example, specific distributions are given a value such as 0 (for uniform distributions) and 1 (for nonuniform distributions). The raw data is then associated with their distributions, and the neural network is trained from this data set. New data is then fed into the neural network, which returns either a 0 if the distribution is determined to be uniform, or 1 if the distribution is determined to be nonuniform.

In another example, there may be a need to decipher between many types of distributions, such as those shown in FIGS. 4A-4E. In this case, each distribution is given a numeric category identifier (such as integer values between 1 and 5, if there are 5 different categories). Each raw data measurement is associated with a specific category identifier depending on the distribution, and the neural network is trained. New data tested with the neural network is fed through, and the neural network returns the category value. The output layer of the neural network can also be customized to produce a probability array. Each element in the array (element 1 through 5, as in the previous example) gives a probability that the new data belongs in that category. The new test data is then categorized by the index of the highest probability in the output array.

Under most circumstances of interest, the algorithm cannot provide negative values for the concentration of the retentate. It may be possible that, under some circumstances, an algorithm that is used to determine the distribution of the retentate, could generate locally negative concentrations of the retentate. Techniques, such as non-negative matrix factorization, can be used to modify the algorithm generated using the neutral network to prevent negative values for the retentate concentration.

Thus, the radio frequency control unit 122 is adapted to generate data in response to the changes in the characteristics of the radio frequency signals that are representative of the one or more states of the radio frequency sensor system 102 and the machine learning system includes a neural network 125 comprising an input 127 for the data, a processing unit 129 for the data, and a numeric output 131 representative of the one or more states of the radio frequency sensor system 102.

More specifically, in one embodiment, the system 102 comprises a retentate filter 106 or 108 in the housing cavity 104 and the radio frequency control unit 122 is adapted to generate data in response to the changes in the characteristics of the radio frequency signal representative of changes in the state of the retentate filter 106 or 108.

Still more specifically, in one embodiment, the radio frequency control unit 122 is adapted to generate data in response to the changes in the characteristics of the radio frequency signal representative of changes in the distribution of retentate in the retentate filter 106 or 108.

In another example, the neural network may be utilized to identify different operation states of SCR catalysts or other catalysts 106 or 108 in the system 102. A neural network algorithm would be able to determine the subtle differences in the RF measurements for a catalyst 106 or 108 operating at its normal state versus when it has undergone extended thermal aging or poisoning with sulfur or another deactivation agent. Historically, such conditions have been identified by subtle changes in the phase or magnitude measurements of these systems.

Thus, in one embodiment, the system 102 comprises a catalyst 106 or 108 in the housing cavity 104 and the radio frequency control unit 122 is adapted to generate data in response to the changes in the characteristics of the radio frequency signal representative of changes in the state of the catalyst 106 or 108.

More specifically, in one embodiment, the measured quantity may be the amount of one or more exhaust constituents stored or adsorbed on the catalyst 106 or 108 or interacting with the catalyst 106 or 108 in some way, such as by poisoning in another example.

Examples of these changes include a shift in the frequency or amplitude of a resonant mode or anti-resonant mode (trough or valley shown in FIG. 2A) or a shift in phase at a given frequency or over a predefined frequency range. Although difficult to detect by manual inspection or analysis, a neural network is specifically well suited to identify and flag these variations.

Of particular interest is fault and failure detection of the filter or catalyst 106 or 108, or other such systems. Much of the complexity in aftertreatment control, specifically, is the need to fulfill primary and redundancy requirements for on-board diagnostics (OBD). Without inspecting the specifics of the RF signal, a failed part, such as a faulty cable, or a cracked or missing substrate, or degraded catalyst 106 or 108 might result in state measurements within the tolerances of the system 102. A neural network trained to identify these failures provides an additional tool in failure diagnostics, as well as improve overall measurement accuracy. Further, the measurement quality is improved by utilizing neural network to detect and compensate for variations in the signal due to part-to-part variation, residual moisture at startup and low temperature operation, as well as detection of morphological changes to the constituents of the combustion process, such as soot or any other resulting species.

In terms of computation, neural networks can become very complex. In a traditional neural network, each layer involves a series of multiplication and addition computations, followed by computation through a basis function.

For example, in a layer with N inputs and m nodes, computation of the output to the next layer first involves a series of N×m multiplications and N×m additions via the first two matrix-based equation equations below, where the second equation is the matrix representation of the first:

$$\text{Output} = X * W + B$$

$$O = [x_1 \ x_2 \ \ldots \ x_N] \begin{bmatrix} w_{11} & \cdots & w_{1m} \\ \vdots & \ddots & \vdots \\ w_{N1} & \cdots & w_{Nm} \end{bmatrix} + [b_1 \ b_2 \ \ldots \ b_m]$$

$$S(o_i) = \frac{e^{o_i}}{e^{o_i} + 1}$$

Following this initial computation, each of the n nodal outputs is passed through a basis function either by direct computation or via lookup table. An example of a typical basis function is the sigmoid function $S(o_i)$ represented in the third equation above. Following computation of the output through the basis function, each output from any given layer is then used as the input to the next layer, with the full neural network having multiple layers. As such, there is an advantage to reducing the dimension of the neural network, as doing so will also reduce the total number of computations that are required to achieve an output, and therefore reduce the computing time and resources required to both store the network and compute outputs from the neural network.

In order to do this, it is important to identify which input features have the largest impact on the effectiveness of the neural network. This can be accomplished in a number of ways. In one example, a Decision Tree algorithm may be used to automatically select the features that most completely categorize the data. These algorithms produce a data flow structure that relies on making yes/no decisions on individual features from the raw data. More features are added to the Decision Tree flow structure until all of the data is appropriately categorized. As such, Decision Tree can be used to determine the smallest number of input features required to fully categorize the data, and is able to return those features for use. The practical benefit is that the neural network can be trained using only the features identified by the Decision Tree algorithm, as opposed to all the features available. In that respect, the dimensionality, and thus the complexity, of the neural network may be reduced. Other algorithms or approaches may be used to increase the computational efficiency or identify the most important parameters.

As a machine learning technique, variations of the Decision Tree algorithm may be utilized to perform detection of different system states in themselves. For example, the use of Random Forest may be used to make real-time categorization decisions about the data. The Random Forest algorithm combines many different Decision Tree algorithms into one processing unit. As such, several trees are "grown" based on the training data, and each tree makes a decision about the test data. The advantage to Random Forest is that it is more robust and, since it is based on many different individual trees, is less susceptible to noise factors introduced in the data. As new data is tested and categorized, the Random Forest may be retrained to adapt to new data. As such, an advanced version of Random Forest may be utilized to train itself with new data using minimal, or no, human guidance. This training may be completed online (on the sensor or attached control unit) or offline on a separate computer.

A third technique for dimensionality reduction is Principal Component Analysis (PCA). In this technique, the raw data of dimension N is decomposed into its principal eigenvectors. The number of eigenvectors is always fewer than N. Once decomposed, the eigenvectors are computed from new raw data measurements and used as the new inputs to neural network. While the computation of the eigenvectors is somewhat intensive, and some physical intuition of the system is lost, PCA is effective in reducing the dimension of the neural network algorithm.

The eigenvectors themselves may also be used to identify the input features required to fully categorize the data. The principal components are computed via the dot product of the input data with the eigenvector. The eigenvector itself is an N×1 weighting vector, whereby the most important features may be determined by selecting only those features with the highest absolute weights in each eigenvector. With this method, PCA may be utilized to identify only the most important features in the original data, thus enabling development of neural networks with reduced-order and complexity. Additionally, the key features are known, which gives additional physical understanding.

Another means for reducing the complexity and size of neural networks, in addition to simplifying the training process, is to down-select the parameters used to train the network based on the underlying physical principles. In one example the calibration of an RF sensor used to monitor soot and ash loading of a particulate filter using neural networks may be simplified by selecting only those resonances (or any other signal features shown in FIG. 2) to be relevant to the specific regions of interest within the cavity, as illustrated by the electric field distributions shown in FIGS. 3A-3D. In this manner, the size of the training data set is significantly reduced. This same approach may be applied to monitor ammonia storage on a particulate filter or oxygen storage on a three-way catalyst, for example.

Figure 5A:
FIGS. 5A and 5B are flow charts of the data flow structure and the steps required to successfully train and implement the neural network of the machine learning system of the emissions aftertreatment RF sensor system of the present invention.

In another example, the down-selection process is performed via a secondary machine learning system or method. One example of this process is outlined in FIG. 5A. Features may be selected based on their relevance to the physical resonance structure as shown in FIGS. 3A-3D. Oftentimes the number of relevant features is still quite large. To further down-select the parameters for use in a neural network, a secondary selection process such as Decision Tree may be used. This process creates a hierarchy of the parameters in order of their relevance to determining the output by computing the correlation of each parameter individually with the output. The neural network may then be trained based on a smaller subset of the preselected features. The number of features utilized relies on the desired accuracy level of the final neural network.

Figure 5B:

In another example, the feature identification and down-selection processes is reversed to determine the most relevant parameters for use in the neural network. An example of this process is shown in FIG. 5B. In this example, the dimension is first reduced by decomposing the RF measurement into its principal components via the eigenvectors of the entire data set. This process is known as Principal Component Analysis (PCA). Each principal component is a vector of the same length as the original measurement, and consists of the weighting factor applied to each feature. As such, the relative magnitude of each index in the principal component is related to the importance of that particular feature in determining the output of the neural network. By selecting the features from the original data set that have the highest absolute weights in the principal component, the features with the highest relevance may be selected.

Figure 6A:
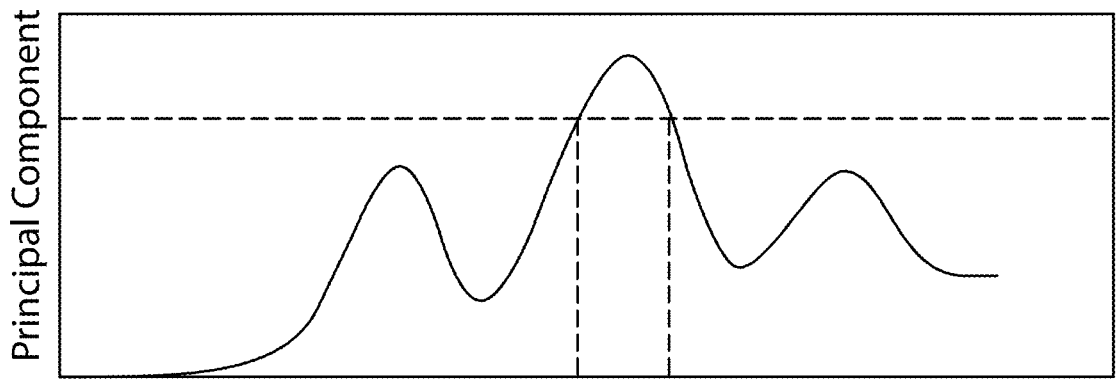
FIGS. 6A and 6B are charts depicting a simple principal component and how the characteristics of that component enable identification of important features of the RF spectrum for use in training and evaluating of the neural network of the machine learning system of the emissions aftertreatment RF sensor system of the present invention.
Figure 6B:
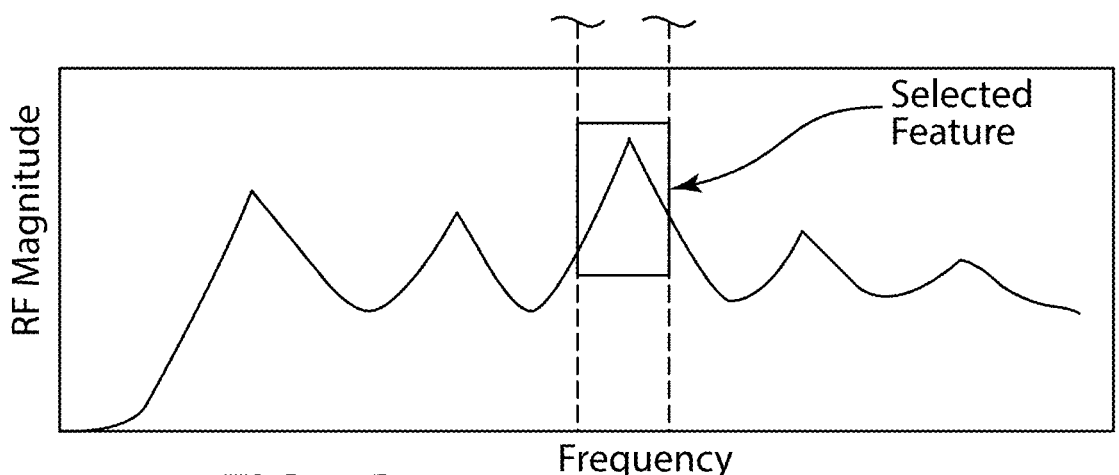

A representation of this selection process is shown in FIGS. 6A and 6B. This may be accomplished by selecting features from one or several principal components. By reducing the order of the neural network first by determining the principal components, and then selecting the most relevant features based on those components, features may be selected without losing a physical understanding of the process, and the selected features may be tied directly to physical resonances and characteristics of the RF signal.

In another example, additional sensor inputs such as inputs from sensors or probes 114, 116, 118, or 120 shown in FIG. 1 or any other system inputs such as other sensors, or simulated (modeled) inputs, or inputs stored in a reference or lookup table are selected for inclusion in the neural network training, but only if those inputs relate to a relevant physical parameter which may influence the RF signal. Examples of relevant inputs for the particulate filter or catalyst system 102 include temperature, flow rate, operating state of the engine (warm-up or shut-down), urea dosing (in the case of an SCR), or PM: NOx ratio in the case of a particulate filter, among others. Inputs to the training data set may be actual measurement data, or computed or modeled (simulation data) from physical models.

The benefits of restricting the inputs to the machine learning system to only those that are physically relevant to the system 102 are twofold. First, it restricts the size and complexity of the training data set. Second, it eliminates the possibility of establishing correlations between parameters which may be physically unrelated, but exhibit a correlation only in very specific instances, but would not yield a robust calibration over a wide range of real-world conditions. In other words, combining a physical understanding of the system 102 with machine learning (hybrid approach) may result in a more efficient training process and a more robust output.

In one real example, data was collected using a diesel particulate filter 106 or 108 (DPF) loaded with soot in five unique distributions. These distributions are shown in FIGS. 4A-4E and include respectively a uniform distribution (FIG. 4A) as well as outer (FIG. 4B), center (FIG. 4C), semi-cylinder (FIG. 4D) and bilateral (FIG. 4E) distributions. Given that the distribution of each measurement is known in advance (reference states), the measurement set is separated into training and testing data. These subsets are kept mutually exclusive and the separation is performed randomly. The testing data, along with the assigned category, is used to train the neural network, and the testing data is used to generate a category. The category generated from the neural network is compared to the assigned category for determination of test accuracy.

The results of these proof-of-concept experiments are shown in the chart of FIG. 8 which includes a summary of the data used to train and to test is shown in the table along with the overall testing accuracy level.

In the example as shown in FIG. 8, a neural network was trained in order to classify measurements of a DPF filter 106 or 108 in terms of the soot distribution contained within. The five distributions shown in the table above represent the five distributions shown in FIGS. 4A-4E. A subset of RF data collected using these five soot distributions was utilized to train a neural network with the goal of classifying new measurements of DPFs 106 or 108 into one of the soot distribution categories. In this example, 9852 total measurements of each of the distributions were used to train the neural network, which had a dimensional size of 89, meaning that 89 features of the RF data were used as inputs to the neural network. The remaining data, which was not utilized for training purposes, was utilized to test the accuracy of the neural network. In this example, 2463 total measurements of each of the distributions were used to test the pretrained neural network. It was found that this network had an overall accuracy of 100%. For training and output classification purposes, the distribution is described by the class number, as shown in the first column of the table in FIG. 6.

The confusion matrix as shown in FIG. 9 provides the success of the testing performed with the neural network.

The confusion matrix is a summary of the output of the neural network as compared with the actual distribution class. The goal for a confusion matrix is to maximize the classification along the diagonal—this implies that the test categorized the data into the same category that it belongs. Off-diagonal classification implies that the data was classified into a different category.

As can be seen from the confusion matrix in FIG. 9, all of the data was categorized correctly along the diagonal. This gives an overall accuracy of 100%, shown in the blue box in the lower right corner. In this real example, data was used to train and test the neural network model offline (using a computer offline from the actual application). Following application of the neural network offline, the neural network so developed (or a transfer function or calibration function developed from the neural network) may be installed on the sensor control unit so that classifications can be made as new data are collected on application. New test data and its classification may be fed back through the neural network in order to refine or retrain it during live operation.

Knowing the type of distribution using the machine learning system of the present invention can provide a second advantage. Increasingly, information about local loading or storage levels is needed to ensure proper control of filter or catalyst systems. Utilizing information about the retentate distribution along with the global loading level measurements of local loading or storage levels can be obtained. This can be performed by applying a correction factor to the global loading level based on the type of distribution identified. In this way, users can know what the local loading or storage level is and take corrective actions as appropriate. In one example, the corrective action may involve regeneration of the filter or a diagnostic message related to the aging of a catalyst. In another example, the corrective action may involve sending a fault code or triggering a fault indicator such as a MIL lamp.

Figure 10:
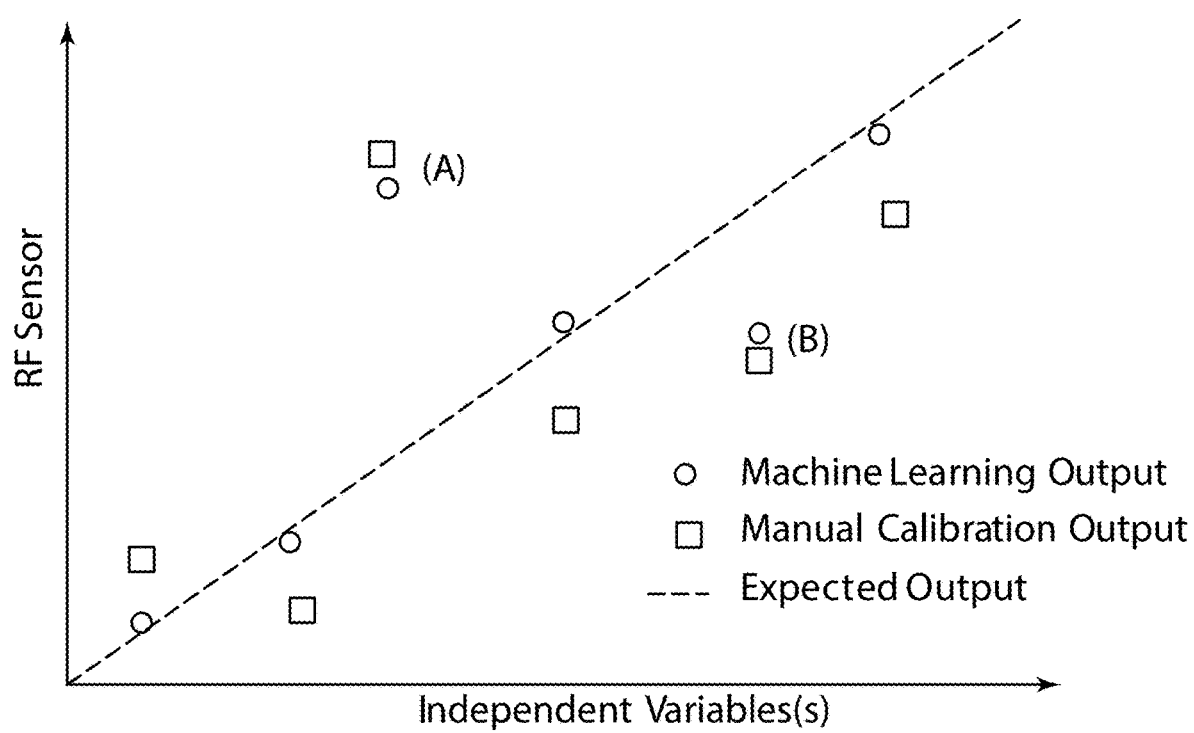
FIG. 10 is a graph comparing the output of the RF sensor system of the present invention against the output of an RF sensor system using a manual calibration method.

FIG. 10 shows a further example illustrating the improvement in performance utilizing the machine learning system of the present invention relative to a manual calibration process. In particular, FIG. 10 shows the correlation between the RF sensor output and one or more independent variables. In one example the independent variable may be time. A large amount of error or variation is observed in the data using the manual calibration. In contrast the RF sensor output using the machine learning system of the present invention exhibits much less error and is closer to the expected output for nearly all cases, with the exception being cases (A) and (B) as shown in FIG. 10.

In FIG. 10, cases (A) and (B) appear as random error in the output for the manual calibration, which is consistent with the error observed in the other data points for the manual calibration cases as well. On the other hand, cases (A) and (B) are observed to be outliers in the machine learning output. In these outlier cases however, application of the machine learning system and method of the present invention is accurately able to classify the outliers (A) and (B) as the result of a fault condition, non-uniform distribution, or some other abnormal condition, similar to the example showing the classification of soot distribution in FIGS. 5 and 6.

In one example, measurement (A) corresponds to a greater than expected response and may be due to elevated engine-out emissions in one example, such as soot, NOx, O2, water or any other emissions constituent.

In another example measurement (B) corresponds to a less than expected measurement which may be due to a failure of the emissions filter or catalyst 106 or 108 allowing emissions to escape or pass through the system 102 rather than accumulated on the system 102.

In yet another example the failure of the emissions system 102 may be due to a physical defect or damage such as a crack, melted, or missing portion of the system 102, or a chemical change such as poisoning or deactivation of a catalyst 106 or 108 in another example. The example shown in FIG. 10 illustrates the benefits of the machine learning system and method of the present invention to not only improve the RF sensor output (decrease error) for normal or typical operating conditions, but also to identify and classify abnormal conditions, such as the outliers shown in points (A) and (B) in FIG. 10.

Although the description addresses the non-uniform distribution in a DPF, SCR, GPF, SCR+F or 3-way catalyst 106 or 108, the machine learning system and method of the present invention can be used in any embodiment where the RF response varies with condition within the cavity 104. For example, in a chemical reactor, temperature inhomogeneities can be measured if the dielectric constant of the catalyst or the substrate vary with temperature. Similarly, flow maldistributions through a catalyst bed can be determined if the dielectric constant of the catalyst or the substrate vary with flow. In this and other cases, materials can be added to the cavity 104 that generate a known response on its dielectric constant due to changes in conditions in the cavity 104. The material does not serve a function separate from that of providing dielectric constant sensitivity to changing conditions in the cavity, which can aid in the development of calibrations utilizing machine learning techniques (eliciting a known response from the system to a change in state or external stimulus) or enhance the accuracy of the measurements.

The machine learning system and method of the present invention may be applied offline or on-line. Offline applications refer to the collection of RF measurements with a sensor on the intended application prior to analysis of the resulting data using conventional computers or other computational systems remote from the actual application, such as in a laboratory or computational data center. Following the offline analysis, the resulting calibration or transfer functions developed from the application of machine learning may be flashed to or programmed in the sensor.

On-line applications include the implementation of the machine learning system and method on the application directly either within the RF control unit 122 or in a separate control unit connected to the sensors. On-line application of these techniques enables a system to be self-learning, that is optimize itself as new data becomes available, and even develop full calibrations without the need for or with minimal external intervention.

In one example, control unit 122, shown in FIG. 1, may be used to train or calibrate the system (self-calibration) on the actual application. In one embodiment, the control unit 122 may be deployed on an application with only a minimal calibration, such as a single point calibration in one example or a two-point calibration spanning the minimum and maximum values in another example. As additional data are collected over varying conditions, the system 102 can apply the machine learning system and method of the present invention to continually update the training data set and improve the calibrated output.

Numerous variations and modifications of the embodiments described above may be effected without departing from the spirit and scope of the novel features of the invention. It is to be understood that no limitations with respect to the machine learning system and method applied to the radio frequency measurements described herein are intended or should be inferred.

What is claimed is:

1. A radio frequency sensor system comprising:
   a housing defining a radio frequency resonant cavity;
   one or more radio frequency probes in the cavity of the housing for transmitting and/or receiving radio frequency signals;
   a radio frequency control unit in communication with the one or more radio frequency probes for determining one or more states of the radio frequency sensor system based on changes in the characteristics of the radio frequency signals; and a machine learning system in communication with the radio frequency control unit for identifying and developing transfer functions and calibrations signals and determining the one or more states of the radio frequency sensor system based on the changes in the characteristics of the radio frequency.

2. The system of claim 1 wherein the state of the radio frequency sensor system is determined based on changes in the amplitude and/or shifts in the frequency and/or shifts in the phase of the radio frequency signals, the machine learning system identifying and developing transfer functions and calibrations based on the changes in the amplitude and/or shifts in the frequency and/or shifts in the phase of the radio frequency signals.

3. The system of claim 2 wherein the radio frequency signals are transmitted and/or received over a broad frequency range for establishing one or more resonant modes, the machine learning system identifying and developing transfer functions and calibrations based on changes in the characteristics of the one or more resonant modes.

4. The system of claim 3 wherein the radio frequency control unit is adapted to generate data in response to the changes in the characteristics of the radio frequency signals that are representative of the one or more states of the radio frequency sensor system and the machine learning system includes a neural network comprising an input for the data, a processing unit for the data, and a numeric output representative of the one or more states of the radio frequency sensor system.

5. The system of claim 4 further comprising a retentate filter or a catalyst in the cavity of the housing, the radio frequency control unit being adapted to generate data in response to the changes in the characteristics of the radio frequency signal representative of changes in the state of the retentate filter or the catalyst.

6. The system of claim 5 wherein the radio frequency control unit is adapted to generate data in response to the changes in the characteristics of the radio frequency signal representative of changes in the distribution of retentate or exhaust constituents in the retentate filter or the catalyst respectively.

7. The system of claim 4 further comprising means for training the neural network to down-select one or more radio frequency sensor system parameters selected from temperature, flow rate, radio frequency resonance modes, radio frequency phase curves, or system operating state.

8. The system of claim 1 further comprising dimensionality reduction means for simplifying the machine learning system transfer functions and calibrations.

9. The system of claim 4 further comprising means associated with the machine learning system for down-sampling a whole set of the data generated by the radio frequency control unit prior to feature selection.

10. The system of claim 1 further comprising means for developing the machine learning system transfer functions and calibrations prior to or during the operation of the system.

11. A method of operating a radio frequency sensor system including a housing defining a radio frequency resonant cavity, one or more radio frequency probes in the cavity of the housing for transmitting and/or receiving radio frequency signals, and a radio frequency control unit in communication with the one or more radio frequency probes for determining one or more states of the radio frequency sensor system based on changes in the characteristics of the radio frequency signals comprising the step of providing a machine learning system in communication with a radio frequency control unit for identifying and developing transfer functions and calibrations and determining one or more states of the radio frequency system based on changes in the characteristics of radio frequency signals transmitted and/or received in a cavity of the radio frequency sensor system.

12. The method of claim 11 wherein the state of the radio frequency sensor system is determined based on changes in the amplitude and/or shifts in the frequency and/or shifts in the phase of the radio frequency signals, the machine learning system identifying and developing transfer functions and calibrations based on the changes in the amplitude and/or shifts in the frequency and/or shifts in the phase of the radio frequency signals.

13. The method of claim 12 wherein the radio frequency signals are transmitted and/or received over a broad frequency range for establishing one or more resonant modes, the machine learning system identifying and developing transfer functions and calibrations based on changes in the characteristics of the one or more resonant modes.

14. The method of claim 13 wherein the radio frequency control unit is adapted to generate data in response to the changes in the characteristics of the radio frequency signals that are representative of the one or more states of the radio frequency sensor system and the machine learning system includes a neural network comprising an input for the data, a processing unit for the data, and a numeric output representative of the one or more states of the radio frequency sensor system.

15. The method of claim 14 further comprising a retentate filter or a catalyst in the cavity of the radio frequency sensor system, the radio frequency control unit being adapted to generate data in response to the changes in the characteristics of the radio frequency signal representative of changes in the state of the retentate filter or the catalyst.

16. The method of claim 15 wherein the radio frequency control unit is adapted to generate data in response to the changes in the characteristics of the radio frequency signal representative of changes in the distribution of retentate or exhaust constituents in the retentate filter or the catalyst respectively.

17. The method of claim 14 further comprising the step of training the neural network to down-select one or more radio frequency sensor system parameters selected from temperature, flow rate, radio frequency resonance modes, radio frequency phase curves, or system operating state.

18. The method of claim 11 further comprising the step of dimensional reduction for simplifying the machine learning system transfer functions and calibrations.

19. The method of claim 14 further comprising the step of down-sampling a whole set of the data generated by the radio frequency control unit prior to feature selection.

20. The method of claim 11 further comprising the step of developing the machine learning system transfer functions and calibrations prior to or during the operation of the system.

21. A radio frequency sensor system comprising:
a housing defining a radio frequency resonant cavity;
one or more radio frequency probes in the cavity of the housing for transmitting and/or receiving radio frequency signals;
a radio frequency control unit in communication with the one or more radio frequency probes and adapted to generate data for determining one or more states of the radio frequency sensor system based on changes in the amplitude and/or shifts in the frequency and/or shifts in the phase of the radio frequency signals; and a machine learning system in communication with the radio frequency control unit and including a neural network with an input for the data generated by the radio frequency control unit, a data processor, and an output, the machine learning system being adapted for identifying and developing transfer functions and calibrations and determining the one or more states of the radio frequency sensor system based on the changes in the amplitude and/or shifts in the frequency and/or shifts in the phase of the radio frequency signals.

* * * * *